United States Patent [19]
Adachi

[11] Patent Number: 5,325,133
[45] Date of Patent: Jun. 28, 1994

[54] DEVICE FOR MEASURING A RETINA REFLECTED LIGHT AMOUNT AND A GAZE DETECTING APPARATUS USING THE SAME

[75] Inventor: Toshiya Adachi, Kobe, Japan

[73] Assignee: Konami Co., Ltd., Hyogo, Japan

[21] Appl. No.: 954,765

[22] Filed: Sep. 30, 1992

[30] Foreign Application Priority Data

Oct. 7, 1991 [JP] Japan .................................. 3-259106

[51] Int. Cl.⁵ ............................................. A61B 3/14
[52] U.S. Cl. .................................. 351/209; 345/158; 345/156; 345/157
[58] Field of Search ................ 351/209, 210; 250/221, 250/201.4; 340/705, 706, 709, 980; 345/158

[56] References Cited

U.S. PATENT DOCUMENTS

| | | | |
|---|---|---|---|
| 4,648,052 | 3/1987 | Friedman et al. .................. | 250/221 |
| 4,798,214 | 1/1989 | Haas ................................... | 351/210 |
| 4,891,630 | 1/1990 | Friedman et al. .................. | 340/706 |
| 4,988,981 | 1/1991 | Zimmerman et al. .............. | 345/158 |
| 5,155,516 | 10/1992 | Shindo ................................ | 351/210 |
| 5,218,387 | 6/1993 | Ueno et al. ......................... | 351/210 |
| 5,220,361 | 6/1993 | Lehmer et al. ..................... | 351/210 |
| 5,227,985 | 7/1993 | DeMenthon ....................... | 345/158 |
| 5,231,674 | 7/1993 | Cleveland et al. ................. | 351/210 |

FOREIGN PATENT DOCUMENTS

| | | | |
|---|---|---|---|
| 2382056 | 10/1978 | France ................................ | 351/210 |
| 3-17696 | 1/1991 | Japan ................................. | 345/158 |
| 935072 | 6/1982 | U.S.S.R. ............................ | 351/209 |

*Primary Examiner*—Richard A. Bertsch
*Assistant Examiner*—Howard R. Richman
*Attorney, Agent, or Firm*—Jordan and Hamburg

[57] ABSTRACT

A device for measuring a retina reflected light amount is provided with a light source for emitting a infrared ray, an image pick-up unit for receiving the infrared ray from a light emitting range at the same position as the light source, a reading unit for reading a pupil area from a face image picked up by the image pick-up unit, and an integrating unit for integrating an amount of light represented by signals which are generated by the image pick-up unit and are located at addresses within the read pupil area. This device is applicable to a gaze detecting apparatus, and provides data which can be used in medical and psychological fields.

2 Claims, 4 Drawing Sheets

DEVICE FOR MEASURING A RETINA REFLECTED LIGHT AMOUNT AND A GAZE DETECTING APPARATUS USING THE SAME

BACKGROUND OF THE INVENTION AND RELATED ART STATEMENT

This invention relates to a device for measuring an amount of light reflected by a retina and a gaze detecting apparatus using the same and, more particularly to a gaze detecting apparatus for detecting a gaze of a person in an indirect manner making use of a face image picked up by an image pick-up unit such as a television camera and a retina reflection characteristic to an incident light. The word "gaze" as used herein means the position or direction in which the eye is looking.

Conventionally, a cursor has been moved on a screen of a personal computer, a CAD, and like apparatus with the use of up- and down-keys provided in a keyboard, a mouse, etc. In order to provide a better user interface by reading an intention of the user from his/her gaze, there have also been proposed various apparatuses for detecting a gaze of the user which are attached to a face of the user. Recently, there has been proposed an indirect gaze detecting apparatus which detects the position of a cornea reflected image and a center of a pupil from a face image picked up by a plurality of cameras, and further detects a center of an eye ball from the detected position of the cornea reflected image and center of the pupil. Such an apparatus is disclosed as in Unexamined Japanese Patent Publication No. 2-134130.

The apparatus disclosed in the above publication requires detections of the position of a spot-like cornea reflected image, and the centers of the pupil and eye ball from the face image. Further, a detector for making these detections is required to have exceedingly high level of accuracy. This has caused fabrication of a larger size apparatus and an increase in manufacturing cost.

SUMMARY OF THE INVENTION

In view of the problems of the prior art, it is an object of the invention to provide a retina reflected light amount measuring device for obtaining a pupil position and an intensity of light reflected by a retina based on a picked up face image, and further to provide an inexpensive gaze detecting apparatus having a normal level of accuracy which issued in conjunction with a plurality of retina reflected light amount measuring devices for detecting displacement angles relative to a gaze based on the retina reflected light intensities obtained by the plurality of retina reflected light amount measuring devices and detects the gaze based on the pupil positions and the displacement angles.

Accordingly, the invention is directed to a device for measuring a retina reflected light amount comprising a light source for emitting an infrared ray within a light emitting range; image pick-up mean mounted at the same position as the light source and adapted for receiving the infrared ray from the light emitting range; reading means for reading a pupil area from a face image picked up by the image pick-up means; and integrating means for integrating an amount of light represented by signals which are generated by the image pick-up means and are located at addresses within the read pupil area.

Further, the invention is directed to a gaze detecting apparatus comprising at least three light sources located at three different positions and adapted for emitting infrared rays within the same light emitting range; image pick-up means corresponding to the respective light sources and mounted at the same positions as the respective light sources, the image pick-up means being adapted for receiving the infrared rays from the light emitting range; reading means for reading pupil areas from the face images picked up by the image pick-up means at the respective positions; pupil line calculating means for calculating pupil lines connecting between the pupil areas read by the reading means and the corresponding mounted positions of the image pick-up means; pupil position calculating means for obtain an intersection of the obtained pupil lines as a pupil position; integrating means for integrating an amount of light represented by signals which are generated by the image pick-up means and are located at addresses within the read pupil areas; storing means for storing a characteristic of a retina reflected light amount relative to a displacement angle from a gaze; displacement angle calculating means for calculating displacement angles from the gaze based on outputs of the integrating means and the retina reflected light amount stored in the storing means; and gaze calculating means for calculating the gaze based on the pupil position and the respective displacement angles.

With the retina reflected light amount measuring device thus constructed, when a face of a person is located within the light emitting range so as to be illuminated by the infrared ray, and the infrared ray is projected on to the face, the light reflected by the face is received by the image pick-up means located at the same position as the light source. The pupil area is read from the picked up face image by the reading means. The pupil area is rad by means of a known pattern recognition or by detecting frequency components corresponding to hemoglobin which is abundantly contained in the light reflected by the retina. Subsequently, the level of light received by respective photoelectric conversion elements corresponding to the read pupil area is integrated to obtain an amount of light reflected through the pupil.

With the gaze detecting apparatus thus constructed, when a face of a person is located within the light emitting range so as to be illuminated by the infrared rays, and the infrared rays are projected on to the face from at least three positions, the rays reflected by the face are received by the respective image pick-up means, thereby face images are picked up. The pupil areas are read from the picked up face images by the reading means. The pupil areas are read by means of a known pattern recognition or by detecting frequency components corresponding to hemoglobin which is abundantly contained in the light reflected by the retina. Subsequently, there are obtained the pupil lines connecting between the mounted positions of the respective image pick-up means and the corresponding pupil areas, and further obtained the pupil position which is an intersection of the pupil lines. On the other hand, the level of light received by respective photoelectric conversion elements corresponding to the read pupil area is integrated to obtain an amount of light reflected through the pupil for reach image pick-up means. The displacement angles relative to the gaze are calculated by comparing thus obtained amounts of reflected light with the characteristic of the retina reflected light amount. The gaze is obtained by means of a geometric calculation based on the pupil position and the displacement angles.

BRIEF DESCRIPTION OF THE DRAWINGS

FIG. 4B showing a displacement angle $\alpha 2$ for a measuring device 12. FIG. 4C showing a displacement angle $\alpha 3$ for a measuring device 13, and FIG. 4D showing a displacement angle $\alpha 4$ for a measuring device 14.

DETAILED DESCRIPTION OF PREFERRED EMBODIMENTS OF THE INVENTION

Figure 2:
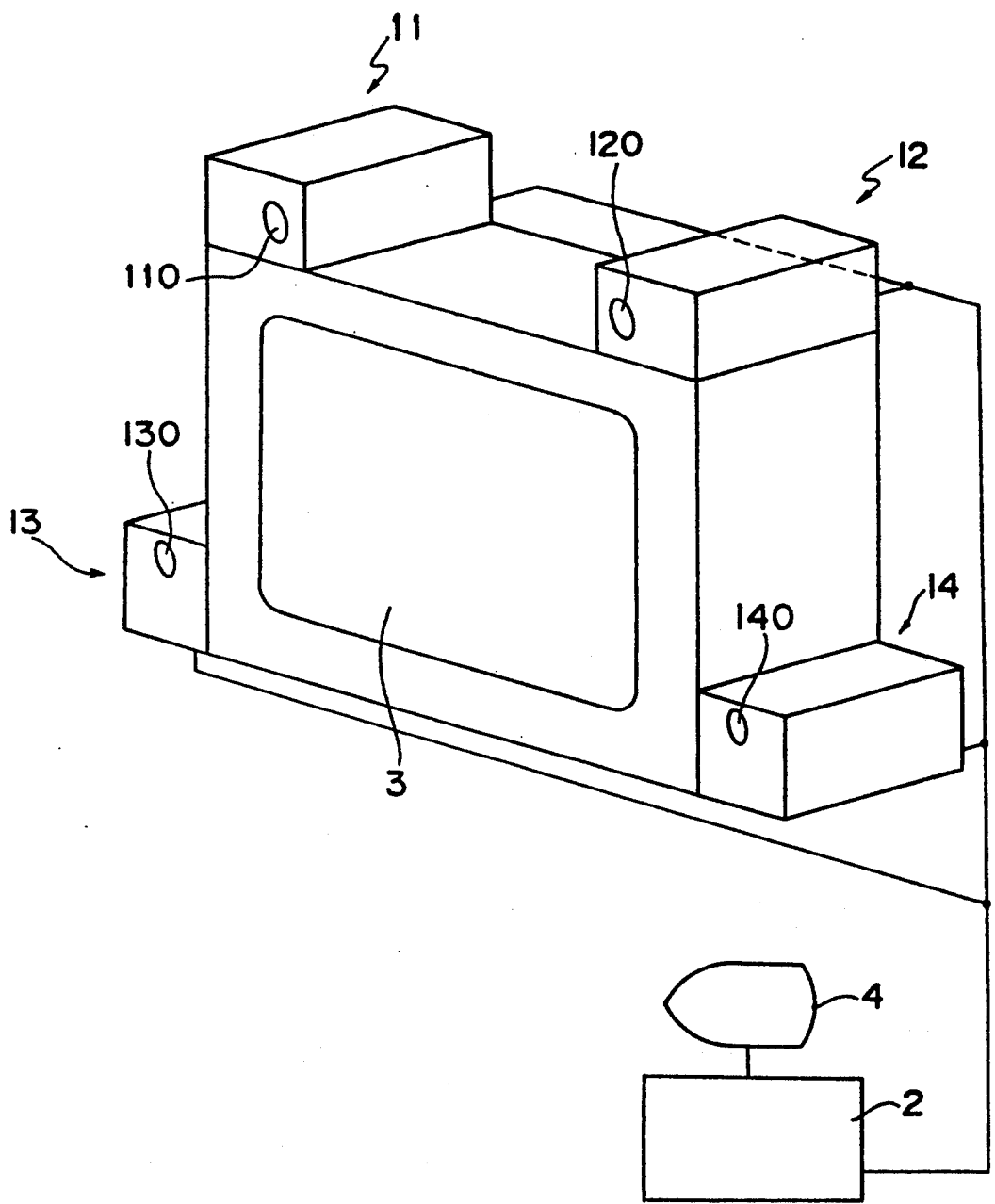
FIG. 2 is a diagram showing an entire construction of the gaze detecting apparatus.

FIG. 2 is a diagram showing an entire construction of a gaze detecting apparatus.

In this figure, indicated at 11 to 14 are measuring devices fixedly arranged in advance at four specified corner positions of a monitor device 3. Thee measuring devices are provided with a light source and an image pick-up unit each. Indicated at 110, 120, 130, and 140 are windows through which projected and reflected lights pass. It is possible to detect a gaze with three measuring devices, but more accurate detection can be conducted with four or more measuring devices.

Indicated at 2 is a computer for detecting the gaze from a face image obtained by the image pick-up unit, and at 4 is a display device for displaying an obtained gaze data in a coordinate system.

Figure 1:
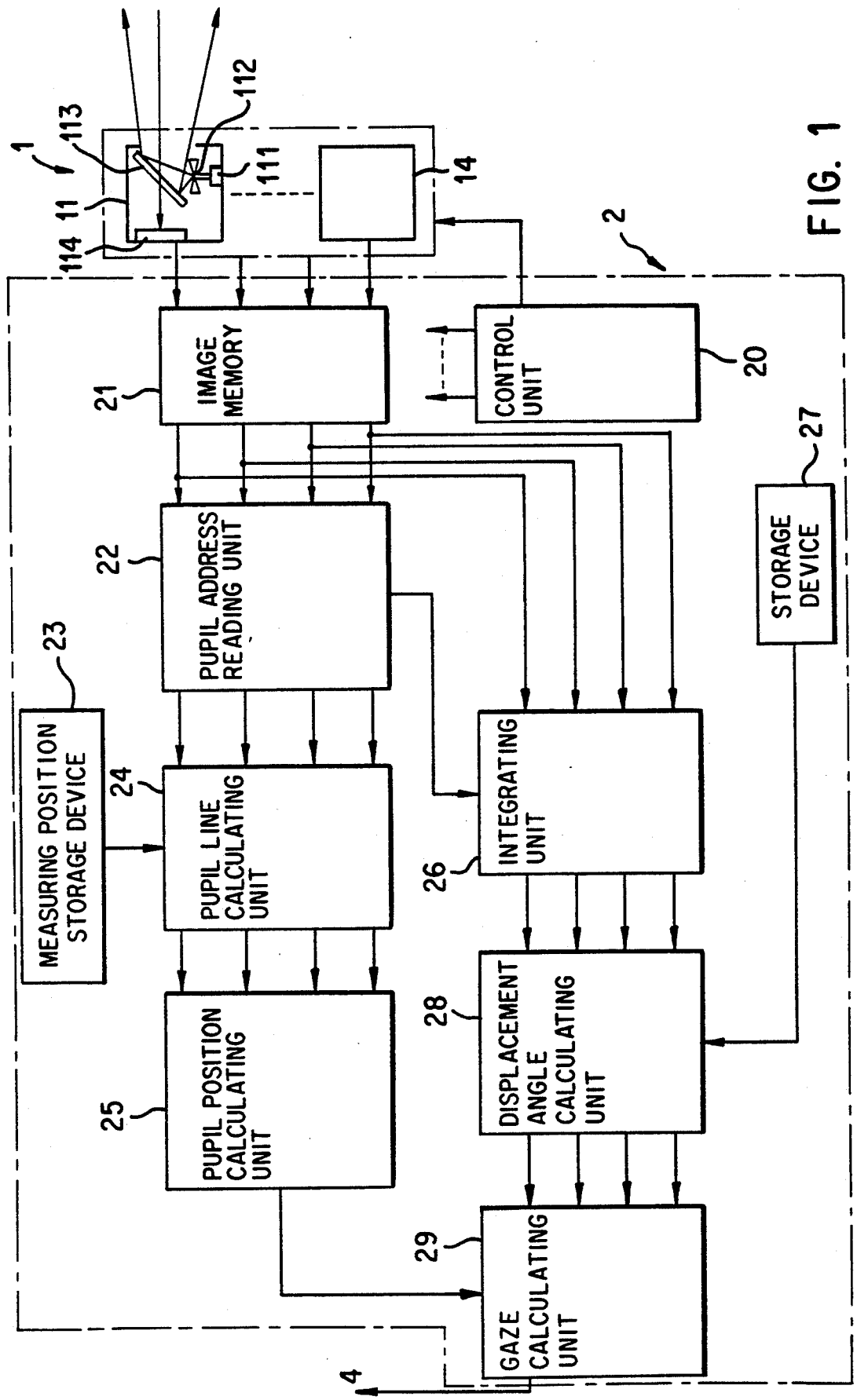
FIG. 1 is a block diagram showing a construction of a measuring device for a gaze detecting apparatus and an interior construction of a computer.

FIG. 1 is a block diagram showing a construction of the measuring devices for use in the gaze detecting apparatus and an interior construction of the computer 2.

A measurement unit 1 includes the measuring devices 11 to 14, each measuring device being constructed identically. The construction of the measuring devices will be described with respect to the measuring device 11. The measuring device 11 is provided with a laser 111 serving as a light source, a concave lens 112 arranged in front of the laser 111 for diffusing the light emitted from the laser 11, and the image pick-up device including a semitransparent mirror 113, CCD 114 (charge couple device), etc. The laser 111 emits specified infrared rays so as not to be influenced by external light. The beam width an the direction of infrared rays emitted from the laser 111 are set within such ranges that the rays illuminate a face of a person located in front of the monitor device 3 even if his/her head moves slightly. The CCD 114 is so constructed as to received the infrared rays emitted from the laser 111 and reflected by the face of the person, and faces in a center direction of a light spread determined by the beam width. The CCD 114 receives the infrared rays which have retuned within the light spread and have passed trough the semitransparent mirror 113. The semitransparent mirror 113 is arranged so as to cause an emitting position and a receiving position of the infrared rays to correspond with each other, thereby eliminating an arrangement error. In this embodiment, the lasers do not emit the infrared rays of the same frequency at the same time, but rather emit the infrared rays of the same frequency sequentially and repeatedly so that the rays emitted from one laser and reflected by a subject should be incident upon the associated CCD and not upon the CCDs not associated with that one laser.

The light emitting direction an the light receiving direction of other measuring devices 12 to 14 are set in such a manner that the light is emitted and received within the same light spread as the measuring device 11. The frequency of the infrared rays in use in the respective measuring devices is preferably the same. However, the respective measuring devices may use the infrared rays of different frequencies. In this case, the infrared rays emitted from one laser cannot be incident upon other three CCDs nor corresponding to that one laser. Accordingly, it is possible for the respective lasers to emit the infrared rays simultaneously.

Indicated at 20 is a control unit for controlling the measuring devices 11 to 14 and devices 21 to 29 to be described later by sending and receiving specified control signals.

Indicated at 21 is an image memory for storing face images picked up by the CCD 114 and CCDs provided in he measuring devices 12 to 14. Indicated at 22 is a pupil address reading units for reading addresses in the image memory 21 where a pupil of the face image is located (pupil addresses) with the aid of, for example, a known pattern recognition technique. In the case where the measuring devices (lasers and CCDs) are so constructed as to emit and receive the light having the wavelength corresponding to hemoglobin, the pupil may be read from the picked up face image by detecting the light having the wavelength corresponding to hemoglobin. This makes use of the following fact. Veins are exposed in a retina, and the light reflected by the retina is magnified by an eye lens and is received by the measuring devices. Accordingly, the received light having reflected by the retina contains higher level of hemoglobin corresponding frequency components compared to the light reflected by other parts of the face, e.g. cheek.

Indicated at 23 is a measuring position storage device for storing information concerning the positions of the respective measuring devices 11 to 14, i.e. mounted positions and directions in which the light is emitted and received. Indicated at 24 is a pupil line calculating unit for calculating pupil lines L1, L2, L3, and L4 connecting between the respective measuring devices 11 to 14 and the pupil of the person based on the positional information from the measuring position storage device 23 and the address information of the pupil read by the pupil address reading unit 22. Pupil lines are lines L1, L2, L3, L4 connecting between the measuring devices 11, 12, 13, 14 and the pupil in FIG. 5. Indicated at 25 is a pupil position calculating unit for calculating an intersection P of the pupil lines L1, L2, L3 and L4 obtained in the pupil line calculating unit 24 as a pupil position.

Figure 3:
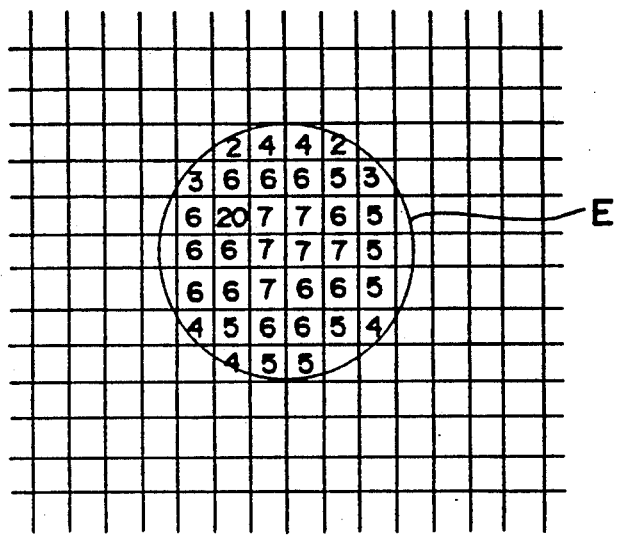
FIG. 3 is a diagram for explaining a received light integrating operation of reading signals located at addresses within a pupil area E from an image memory 21 and integrating received light represented by the read signals.
Figure 4A:
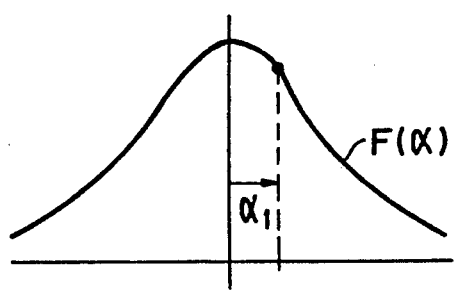
FIGS. 4A, 4B, 4C, and 4D are graphical representations showing a retina reflected light amount characteristic defining relationship between a retina reflected light amount and a displacement angle from a gaze, FIG. 4A showing a displacement angle $\alpha 1$ for measuring device 11.
Figure 4B:
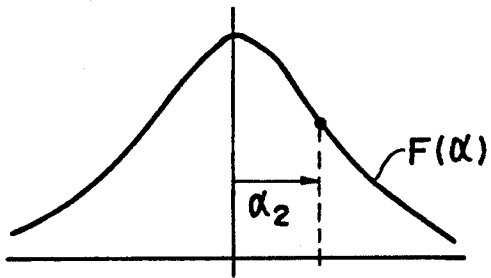
Figure 4C:
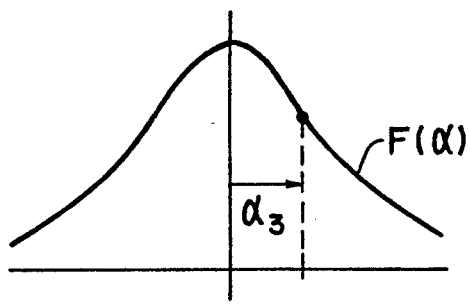
Figure 4D:
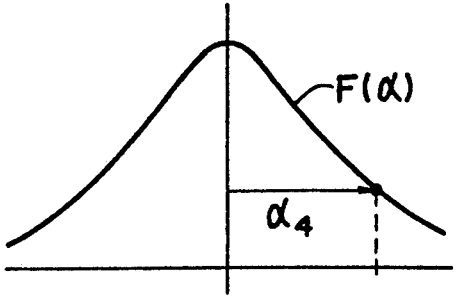

Indicated at 26 is an integrating unit for reading the signals stored at the pupil addresses from the image memory 21 and integrating an amount of received light represented by the rad signals. The integrating operation is carried out by adding all the levels of received light represented by the signals located in the addresses corresponding to an area E within a pupil (pupil area) in the image memory 21 as shown in FIG. 3. The signals representative of the amount of received light (light reception signals) within the pupil area include a signal representative of a considerably high level of light reflected by a cornea, for example, about two to five times as high as the level of light reflected by the retina (this level is indicated as 20 in FIG. 3). Accordingly, the integration accuracy can be improved by removing the signal representative of the light reflected by the cornea from those to be integrated.

Indicated at 27 is a storage device for storing a characteristic of the amount of light reflected by the retina (hereinafter referred to as a retina reflected light amount) relative to a displacement angle $\alpha$ from the gaze. The characteristic of the retina reflected light mount is normalized into levels which are suited to the construction of the apparatus according to the invention. With this conversion, the measurement data can be represented by the levels suitable for the apparatus.

FIG. 4 shows the characteristics of the retina reflected light amount relative to displacement angles $\alpha 1$, $\alpha 2$, $\alpha 3$, and $\alpha 4$ from the gaze. The retina reflects the light through the pupil in the same direction as the light is incident thereupon. The following is known concerning the characteristic of the retina reflected light amount. The reflected light amount is at a maximum level in the direction corresponding with the pupil line. As displaced more from the gaze, the reflected light amount deceases asymptotically as shown in FIG, 4 (for example, such a characteristic is represented by a function $F(\alpha)$ in FIG. 4). It will be appreciated that FIGS. 4A, 4B, 4C, and 4D show amounts of light reflected through the pupil which are received by the measuring devices 11 to 14 respectively.

Figure 5:
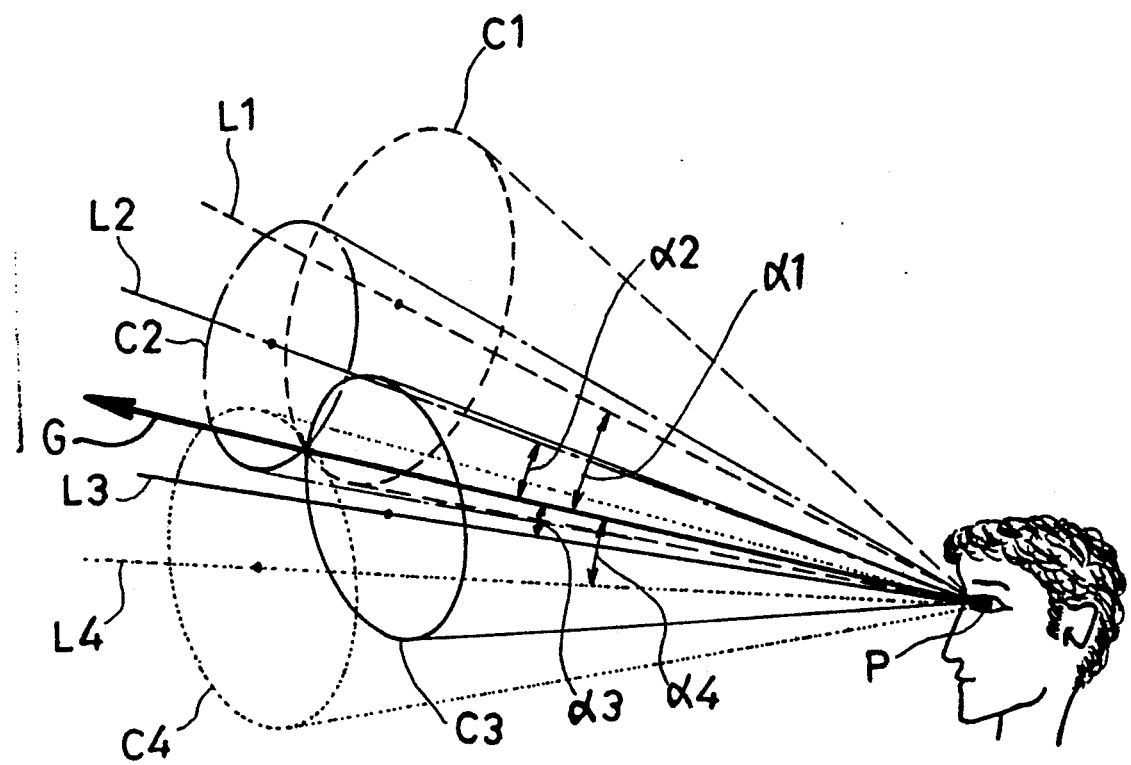
FIG. 5 is a diagram showing cones C1, C2, C3, C4 defined by pupil line L1, L2, L3, L4 and the displacement angles $\alpha 1$, $\alpha 2$, $\alpha 3$, and $\alpha 4$.

Indicated at 28 is a displacement angle calculating unit for calculating the displacement angle $\alpha$ from the gaze based on the characteristic of the retain reflected light amount and the actual amount of received light for each measuring device as shown in FIGS. 4A to 4D. For instance, the displacement angles $\alpha 1$, $\alpha 2$, $\alpha 3$, and $\alpha 4$ are calculated for the respective measuring devices 11 to 14. As shown in FIG. 5, the displacement angles $\alpha 1$, $\alpha 2$, $\alpha 3$ and $\alpha 4$ are the respective angles between the lines extending between the measuring devices 11 to 14 and the pupil P and a line of a sight determined by the direction in which the person is looking, that is, the direction of gaze as represented by the heavy line G in FIG. 5. Indicated at 29 is a gaze calculating unit for calculating cones C1, C2, C3, and C4 based on thus obtained displacement angles $\alpha 1$, $\alpha 2$, $\alpha 3$, and $\alpha 4$ and the pupil position obtained in the pupil position calculating unit 25 as geometrically shown in FIG. 5 and calculating an intersecting line with which all the cones C1 to C4 (four in this embodiment) intersect. In an example shown in FIG. 5, axes of the cones C1, C2, C3, and C4 correspond with the respective pupil lines L1, L2, L3, and L4. The gaze information obtained in the gaze calculating unit 29 is transferred to the display device 4 to be displayed.

It is also possible to display a marker indicating the gaze in the monitor device 3 using the obtained gaze information. With this arrangement, the marker can be moved on a screen of the monitor device 3 while tracking the gaze of the person.

There will be described a gaze detecting operation next.

The infrared rays are emitted from the four lasers simultaneously or sequentially, are reflected by the face of the person, and are received by the respective CCDs. Upon completion of reception of the reflected rays, the image signals obtained in the CCDs are transferred to the image memory 21 to be stored temporarily therein. As well-known, in the CCD, numerous photoelectric conversion elements are arranged in matrix so as to receive the light, which are converted into signals. The converted signals are transferred to corresponding addresses in the image memory 21. Then, the face image data stored in the image memory 21 are compared with specified face images by means of pattern recognition, and the positions of pupils are read from the respective face images. Alternatively, the positions of the pupils may be read by detecting the hemoglobin corresponding frequency components. Further, the pupil line are calculated based on the read positions of the pupils and the mounted positions of the measuring devices, i.e. the measuring position information, and the pupil position which is the intersection P of the obtained pupil lines is calculated.

On the other hand, the levels of the light reception signals at the pupil addresses read by the pupil address reading unit 22 which are located with the pupil area E are integrated, thereby obtaining the amount of light reflected through the pupil and received by each measuring device. Further, the displacement angles $\alpha 1$, $\alpha 2$, $\alpha 3$, and $\alpha 4$ from the gaze are obtained based on the obtained amount of received light and the characteristic of the retina reflected light amount. Thereafter, the cones C1, C2, C3, and C4 are defined based on the obtained displacement angle sand the pupil positions, and the intersecting line with which all the cones intersect is obtained as a gaze information of the person.

Thus obtained gaze information is displayed in the display device 4 or displayed with a marker in the screen of the monitor device 3.

The above operation is repeated in a specified cycle, thereby enabling tracking of the gaze of the person.

Incidentally, in the foregoing embodiment, the displacement angle $\alpha$ is obtained by comparing the characteristic function $F(\alpha)$ of the retina reflected light amount relative to the displacement angle from the gaze stored in the storage device 27 with the actual amount of received light from the pupil. However, since the amount of received light from the pupil differs between individuals, the actually obtained displacement angle $\alpha$ involves an error. Thus, the intersecting line with which all the cones intersect may exist more than one. In this case, the characteristic function $F(\alpha)$ is multiplied by a factor k. The factor k is increased or decreased gradually from 1, and the displacement angle $\alpha$ is newly calculated for each value of k. In this way, there is obtained as intersecting line with which all the cones intersect most closely. By adopting this technique, the displacement angle error caused by the individual difference can be offset.

In the foregoing embodiment, no description is given on how many times the CCD receives the reflected light before sending the light reception signals to the image memory 21. A light receiving operation by the CCD may be conducted only once. Alteratively, a plurality of light receiving operations may be conducted so as to obtain a mean value in light of improvement in measurement accuracy, and the signals representative of the mean value is stored in the image memory 21.

Further, the integrating unit 26 for measuring the retina reflected light amount is capable of measuring the retina reflected light amount based on the data for a single measuring device (including one light source and one image pick-up unit). The retina reflected light amount obtained based on this principle is used as a parameter for the gaze detecting apparatus according to the invention, but it is also used as individual data in the field of medicine. Further, the retina reflected light amount can be used in the field of psychology for measuring a change in the psychological state based on its change over time. In this case, the pupil address reading unit 22 and the integrating unit 26 apply the pupil address reading operation and received light integrating operation to one picked-up face image.

As described above, according to the invention, infrared rays from a light emitting range are received by an image pick-up unit located at the same position as a light source. A pupil area is read from the picked up face image, and the received light represented by the signals located within the pupil area is integrated by an integrating unit. Thus obtained data can be used in the field of medicine and psychology, and can be further used in detecting a gaze of a person.

The infrared rays are emitted from at least three specified positions, are reflected by a face of a person, and are received by the image pick-up units. Pupil positions are obtained based on pupil areas read from signals output from the image pick-up units. Displacement angles from the gaze are obtained based on the amount of light reflected through the pupil which are received by the image pick-up units. The gaze is calculated from the pupil position and the displacement angles. Accordingly, unlike conventional apparatuses, the present invention requires no such exceedingly complicated detection of calculating centers of a pupil and an eye ball based on a spot-like image reflected by a cornea, thereby being capable of providing a gaze detecting apparatus at a reduced cost.

Although the present invention has been fully described by way of example with reference to the accompany drawing, it is to be understood that various changes and modifications will be apparent to those skilled in the art. Therefore, unless otherwise such changes and modifications depart from the scope of the present invention, they should be construed as being included therein.

What is claimed is:

1. An eye detecting apparatus comprising:
   at least three light sources located at three different positions and adapted for emitting infrared rays within the same light emitting range;
   image pick-up means corresponding to the respective light sources and mounted at the same positions as the respective light sources, the image pick-up means receiving the reflected infrared rays reflected from the pupil of a person's eye;
   reading means for reading each respective image pick-up means to provide an output representing pupil areas of images picked up by the image pick-up means;
   pupil line calculating means for calculating pupil lines extending between said pupil areas read by the reading means and each position of each image pick-up means;
   pupil position calculating means for obtaining the intersection of said calculated pupil lines to thereby provide a determination of the pupil position;
   integrating means for integrating the amount of light represented by signals which are generated by each of said image pick-up means and which are located at different positions of the read pupil area;
   storing means for storing characteristic light reflected by the retina relative to a displacement angle, said displacement angle being the angle between the direction of eye gaze and a line extending between the pupil and the image pick-up means;
   displacement angle calculating means for calculating displacement angles based on outputs of the integrating means and the retina reflected light amount stored in the storing means; and
   calculating means for calculating eye gaze based on the pupil position and the displacement angles.

2. An eye detecting apparatus comprising:
   at last three light sources mounted at spaced locations and adapted for emitting infrared rays within the same light emitting range;
   image pick-up means corresponding to the respective light sources disposed at spaced positions and receiving the reflected infrared rays reflected from the pupil of a person's eye;
   reading means for reading each respective image pick-up means to provide an output representing pupil areas of images picked up by the image pick-up means;
   pupil line calculating means for calculating pupil lines extending between said pupil areas read by the reading means and each position of each image pick-up means;
   pupil position calculating means for obtaining the intersection of said calculated pupil lines to thereby provide a determination of the pupil position;
   integrating means for integrating the amount of light represented by signals which are generated by each of said image pick-up means and which are located at different positions of the read pupil area;
   storing means for storing characteristic light reflected by the retina relative to a displacement angle, said displacement angle being the angle between the direction of eye gaze and a line extending between the pupil and the image pick-up means;
   displacement angle calculating means for calculating displacement angles based on outputs of the integrating means and the retina reflected light amount stored in the storing means; and
   calculating means for calculating eye gaze based on the pupil position and the displacement angles.

* * * * *